US009091428B2

(12) United States Patent
Ferguson

(10) Patent No.: US 9,091,428 B2
(45) Date of Patent: Jul. 28, 2015

(54) MEDICAL HEADLAMP ASSEMBLY HAVING INTERCHANGEABLE HEADLAMP TYPES

(71) Applicant: RIVER POINT, LLC, Portland, OR (US)

(72) Inventor: John Thomas Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 60 days.

(21) Appl. No.: 14/162,244

(22) Filed: Jan. 23, 2014

(65) Prior Publication Data

US 2014/0334133 A1  Nov. 13, 2014

Related U.S. Application Data

(63) Continuation-in-part of application No. 14/057,351, filed on Oct. 18, 2013.

(60) Provisional application No. 61/822,493, filed on May 13, 2013.

(51) Int. Cl.
*F21V 33/00* (2006.01)
*F21V 21/084* (2006.01)
*A61B 19/00* (2006.01)

(52) U.S. Cl.
CPC ......... *F21V 33/0068* (2013.01); *A61B 19/5202* (2013.01); *F21V 21/084* (2013.01); *Y10T 29/49117* (2015.01)

(58) Field of Classification Search
CPC .............. F21V 33/0068; F21V 21/084; A61B 19/5202
USPC .................................................. 362/105, 191
See application file for complete search history.

(56) References Cited

U.S. PATENT DOCUMENTS

| 581,129 | A | * | 4/1897 | Nevius ......................... 362/105 |
| 3,830,230 | A | | 8/1974 | Chester |
| 4,516,190 | A | | 5/1985 | Kloots |
| 5,667,291 | A | | 9/1997 | Caplan |
| 5,760,546 | A | | 6/1998 | Pabla |
| 5,926,320 | A | | 7/1999 | Parkyn, Jr. et al. |
| 6,566,816 | B2 | | 5/2003 | Fushimi |
| 6,841,950 | B1 | | 1/2005 | Walker |
| RE39,162 | E | | 7/2006 | Caplan |
| 7,210,810 | B1 | | 5/2007 | Iversen et al. |

(Continued)

FOREIGN PATENT DOCUMENTS

KR  1020110095674 A1  8/2011

OTHER PUBLICATIONS

MedLED, medLED Sapphire O.R. Surgical Headlight System, brochure, medLED//Portable Surgical Lighting, Portland, Oregon United States of America.

*Primary Examiner* — David V Bruce

(74) *Attorney, Agent, or Firm* — Timothy E. Siegel Patent Law, PLLC; Timothy E. Siegel

(57) ABSTRACT

A medical headlamp assembly has a headband subassembly, including an electrical network, including a battery and an electrical jack and a headlamp mount. An electrical headlamp subassembly, has a mounting element that is matingly and removably engaged to the headlamp mount, and an electrical plug that is matingly and removably engaged to the jack and an electrical headlamp, electrically connected to the plug.

19 Claims, 8 Drawing Sheets

(56) References Cited

U.S. PATENT DOCUMENTS

| | | |
|---|---|---|
| 7,671,544 B2 | 3/2010 | Clark |
| 7,737,194 B2 | 6/2010 | Kashiwagi et al. |
| 7,762,698 B2 | 7/2010 | Menze |
| 7,847,302 B2 | 12/2010 | Basin et al. |
| 8,436,542 B2 | 5/2013 | Middleton-White |
| 8,449,132 B2 | 5/2013 | Lau |
| 8,587,213 B2 | 11/2013 | Yee |
| 2005/0117327 A1 | 6/2005 | Gupta |
| 2005/0243558 A1 | 11/2005 | Van Duyn |
| 2006/0098440 A1 | 5/2006 | Allen |
| 2006/0285316 A1 | 12/2006 | Tufenkjian et al. |
| 2007/0097703 A1 | 5/2007 | Goldfain |
| 2009/0207617 A1 | 8/2009 | Merchant et al. |
| 2012/0120635 A1* | 5/2012 | Strong et al. ............ 362/105 |
| 2013/0250593 A1* | 9/2013 | Popper et al. ............ 362/476 |

* cited by examiner

US 9,091,428 B2

MEDICAL HEADLAMP ASSEMBLY HAVING INTERCHANGEABLE HEADLAMP TYPES

RELATED APPLICATIONS

This application is a continuation-in-part of application Ser. No. 14/057,351, filed on Oct. 18, 2013, which is incorporated herein by reference as if fully set forth herein, and which, in turn, claims priority from provisional application Ser. No. 61/822,493, filed May 13, 2013, which is also incorporated by reference as if fully set forth herein.

BACKGROUND

Medical headlamp providers have attempted to make a single design that serves a variety of purposes, and in so doing have diminished the capability of such a design to perform any single specialized purpose. For example, many designs feature an adjustable iris, to permit a user to set the beam width of the light produced. Unfortunately, such an iris blocks a good deal of the light, thereby requiring a brighter light source, needing more power.

It is an undesirable expense, however, to purchase a separate head lamp assembly for each purpose that a physicians' office or hospital department may require. It would be desirable to find a way to eliminate at least part of this expense.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a medical headlamp assembly has a headband subassembly, including an electrical network, including a battery and an electrical jack and a headlamp mount. An electrical headlamp subassembly, has a mounting element that is matingly and removably engaged to the headlamp mount, and an electrical plug that is matingly and removably engaged to the jack and an electrical headlamp, electrically connected to the plug.

In a second separate aspect, the present invention may take the form of a method of switching out a medical headlamp that makes use of a medical headlamp assembly having a headband assembly, including a mounting element, an electrical jack and a power supply assembly electrically connected to the electrical jack. A first headlamp assembly is removably engaged to the mounting element and including a conductor terminating in a plug that is plugged into the jack; and a second headlamp assembly removeably engageable to the mounting element and including a conductor terminating in a plug that is engageable to the jack. The method includes removing the first headlamp assembly from the mounting element and unplugging the first headlamp plug from the jack and mounting the second headlamp on the mounting element and plugging the second headlamp plug into the jack.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
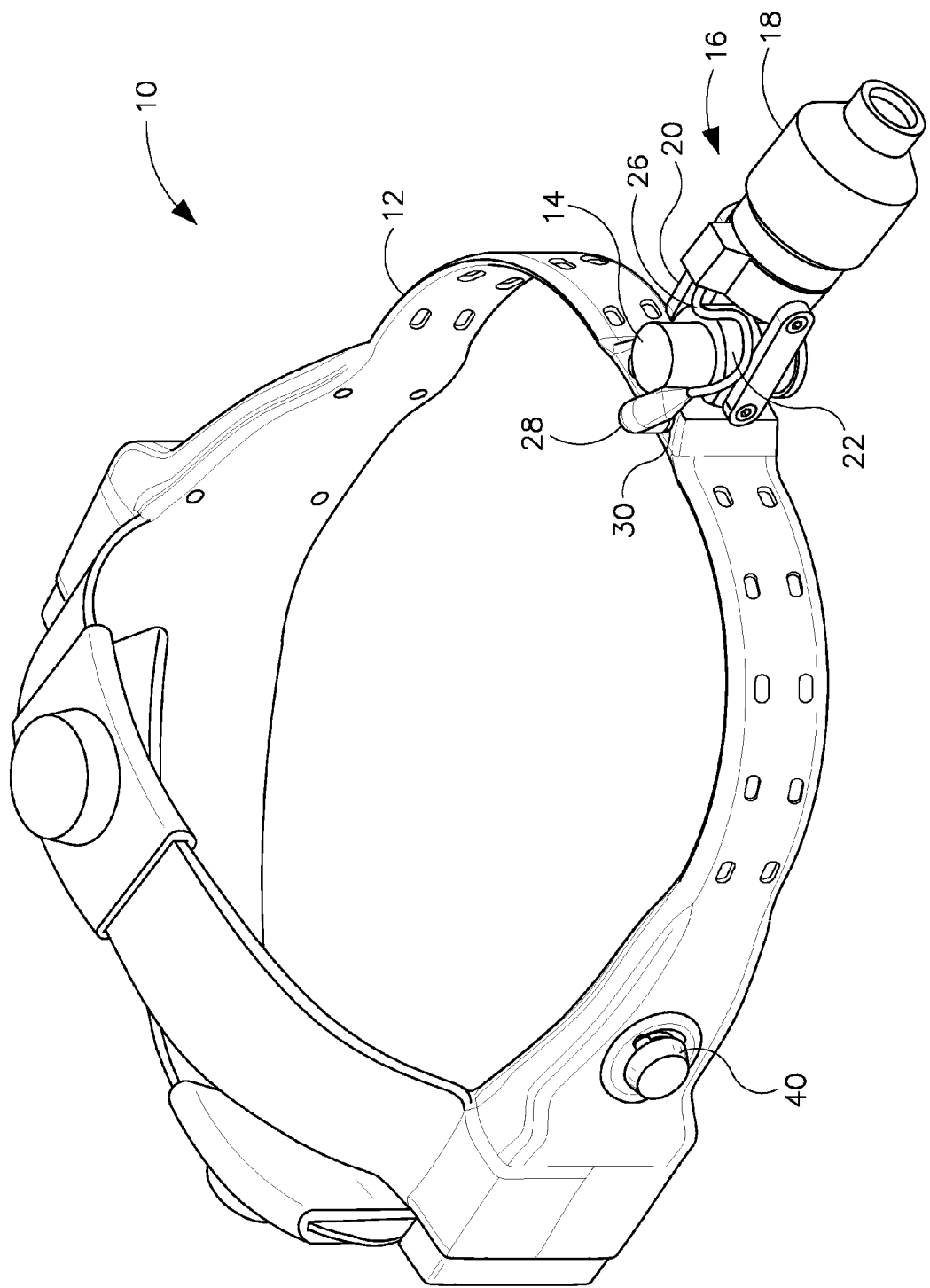
FIG. 1 shows an isometric view of a medical headlamp assembly, having an attached medical headlamp of a first type.

Referring to FIGS. 1-6, in a first preferred embodiment a medical headlamp assembly 10 includes a headband 12, supporting a mounting column 14. A low intensity headlamp assembly 16 includes a low intensity headlamp 18, a linkage 20, a slider 22. Also included is an electrical conductor 26 terminating in a four pole audio plug 28, which plugs into a four pole audio jack 30.

Figure 2:
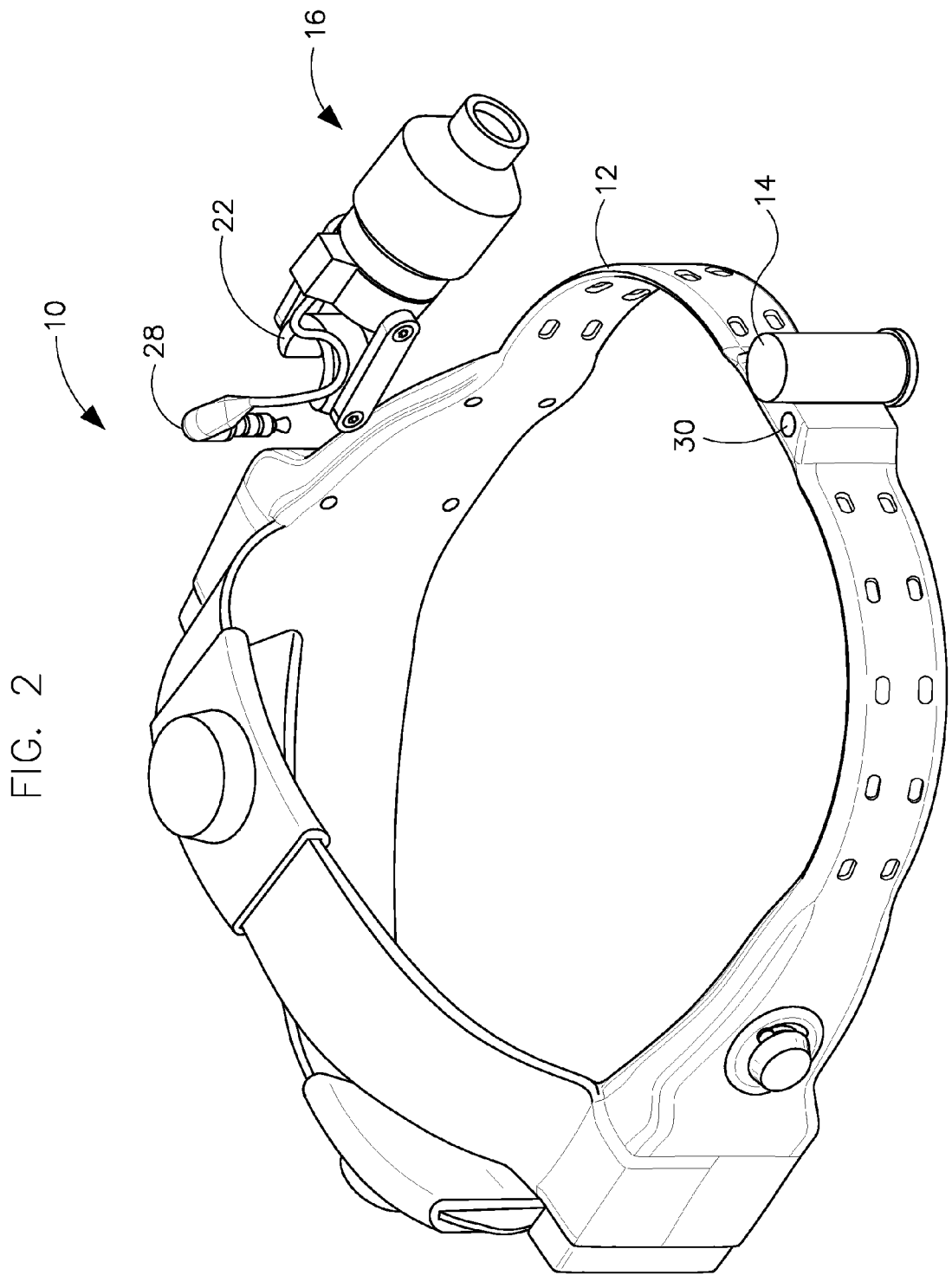
FIG. 2 shows an isometric view of a medical headlamp assembly, having a detached medical headlamp of the first type.
Figure 3:
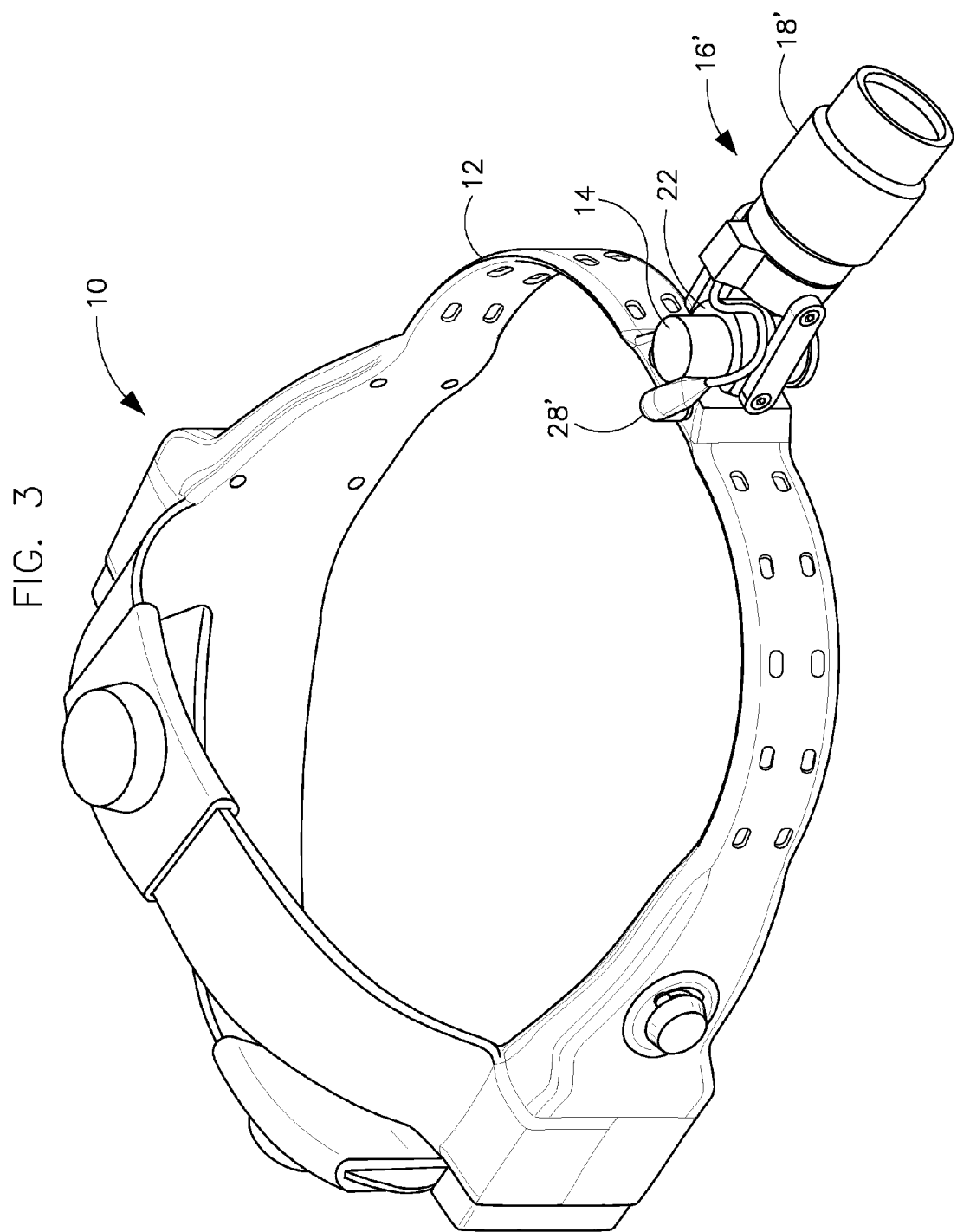
FIG. 3 shows an isometric view of a medical headlamp assembly, having an attached medical headlamp of a second type.
Figure 4:
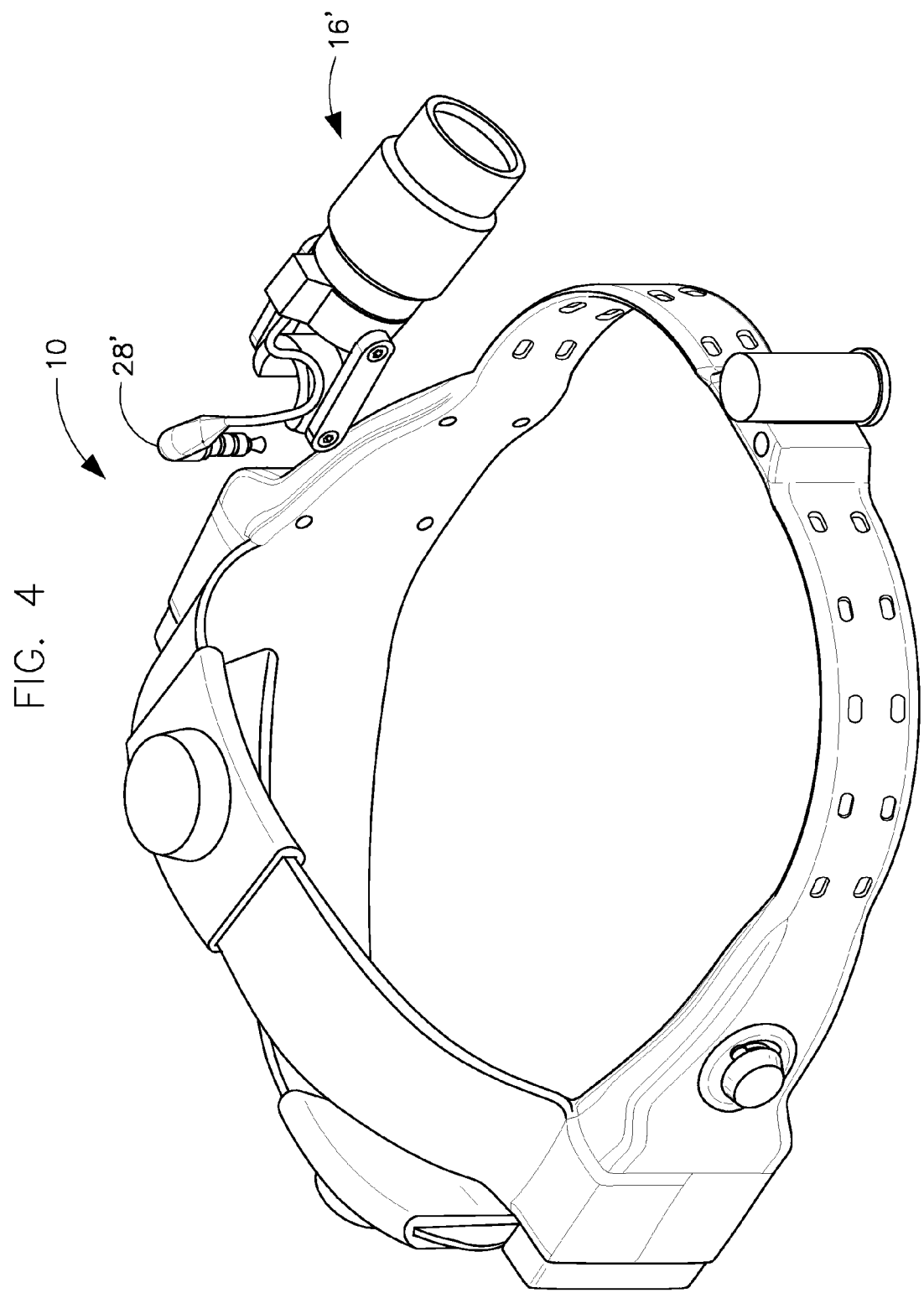
FIG. 4 shows an isometric view of a medical headlamp assembly, having a detached medical headlamp of the second type.
Figure 5:
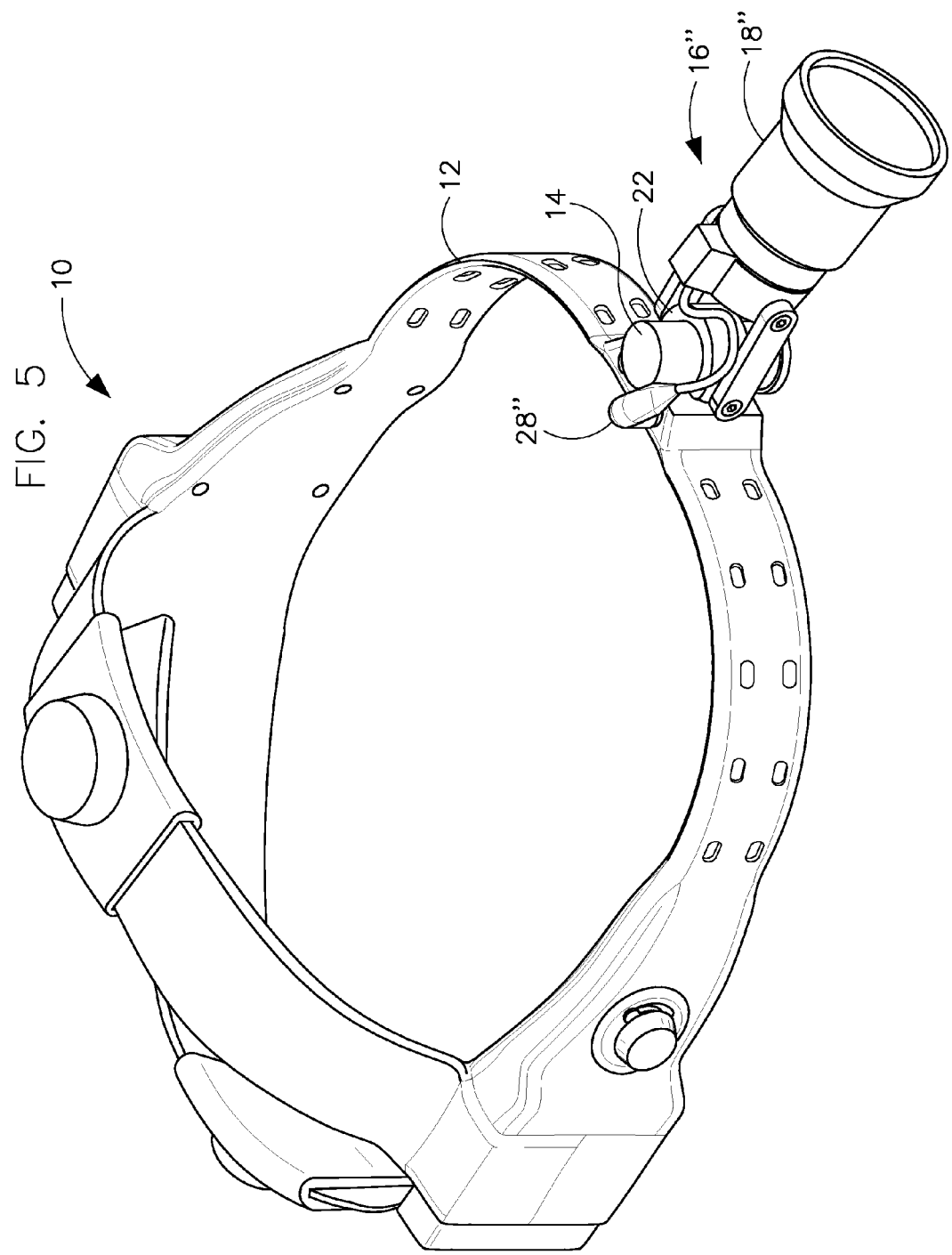
FIG. 5 shows an isometric view of a medical headlamp assembly, having an attached medical headlamp of a third type.
Figure 6:
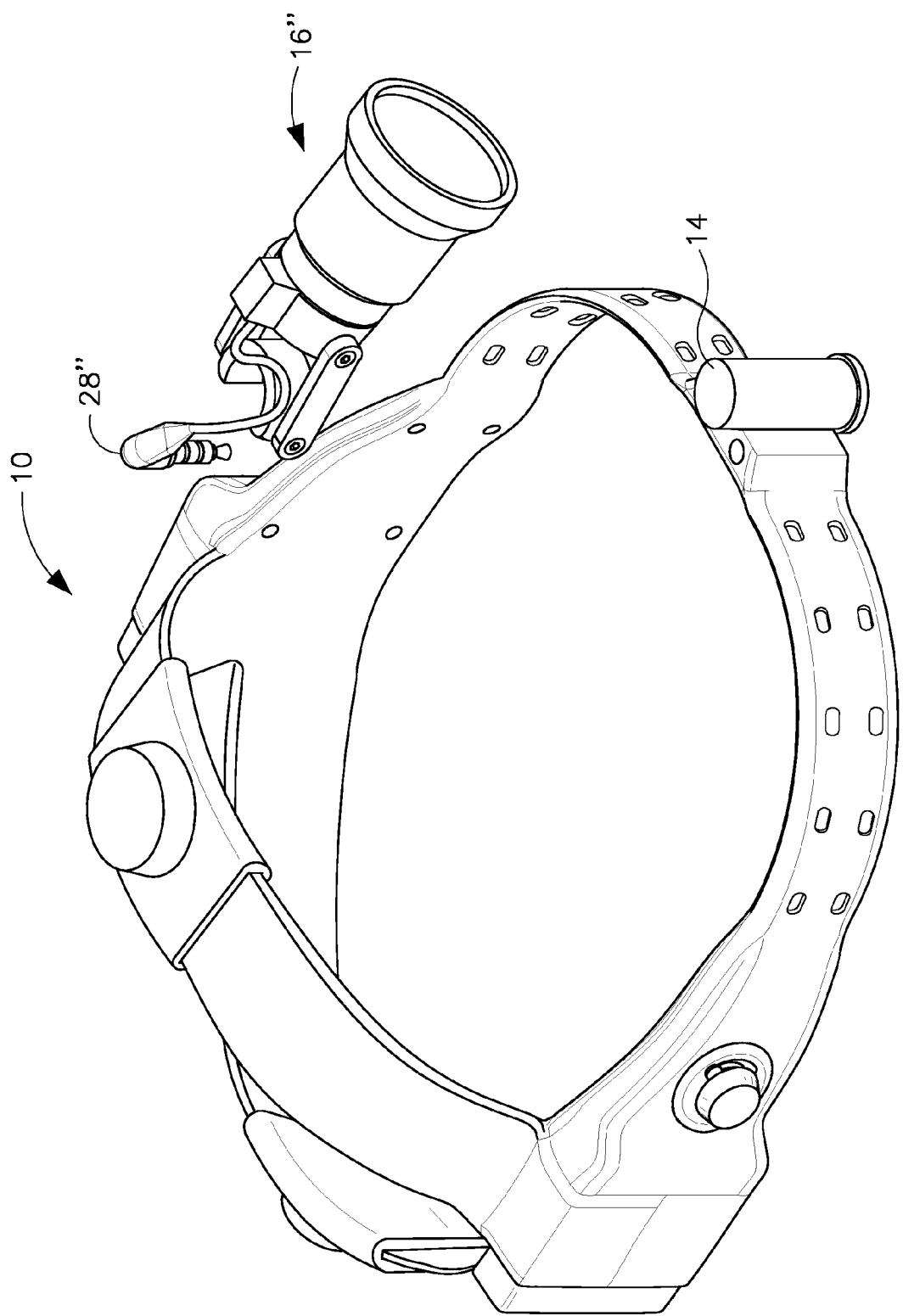
FIG. 6 shows an isometric view of a medical headlamp assembly, having a detached medical headlamp of the third type.

As shown in FIG. 2, when a user decides that he would like to remove assembly 16 from mounting column 14, he pulls assembly 16 upwardly to disengage slider 22 from column 14 and unplugs plug 28 from jack 30. He may do this simply to replace a worn out assembly 16, or (referring to FIG. 3) to install an assembly having different characteristics, such as medium intensity assembly 16', having medium intensity light 18' and plug 28' which is plugged into jack 30. Referring to FIGS. 5 and 6, in like manner assembly 16' can be switched out and assembly 16" having high intensity light 18" and plug 28", can be installed onto with slider 22 on column 14, and with plug 28" plugged into jack 30.

Figure 7:
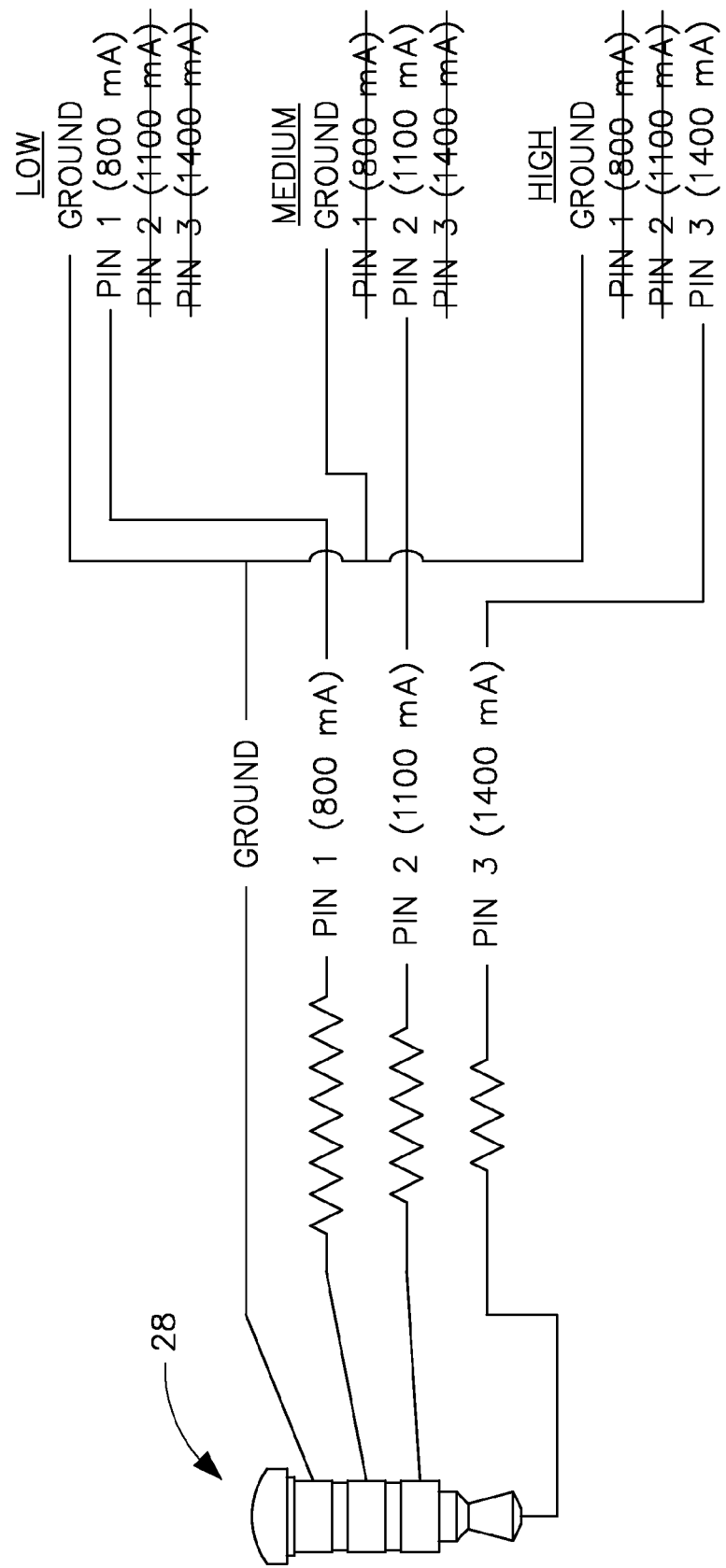
FIG. 7 shows an audio plug and the scheme of use of the poles of the audio plug, that is used in a preferred embodiment of the present invention.

Referring to FIG. 7, although plugs 28, 28' and 28" appear identical, each one has a different active pin (longitudinally arranged electrical contact) that is electrically connected to the light emitting diode (not shown) of lamp 18, 18' or 18", respectively, and serving as the return, with the current being delivered into lamp 18, 18' and 18" in all cases through the ground. Pin 1 of plug 28 serves as the LED return for lamp 18, pin 2 serves as the LED return for lamp 18' and pin 3 serves as the LED return for lamp 18". Pin 1, pin 2 and pin 3 of plug 28 connects to pin 2, pin 3 and pin 4 of jack 30, respectively. Pin 1 of jack 30 connects to the ground of plug 28.

Figure 8:
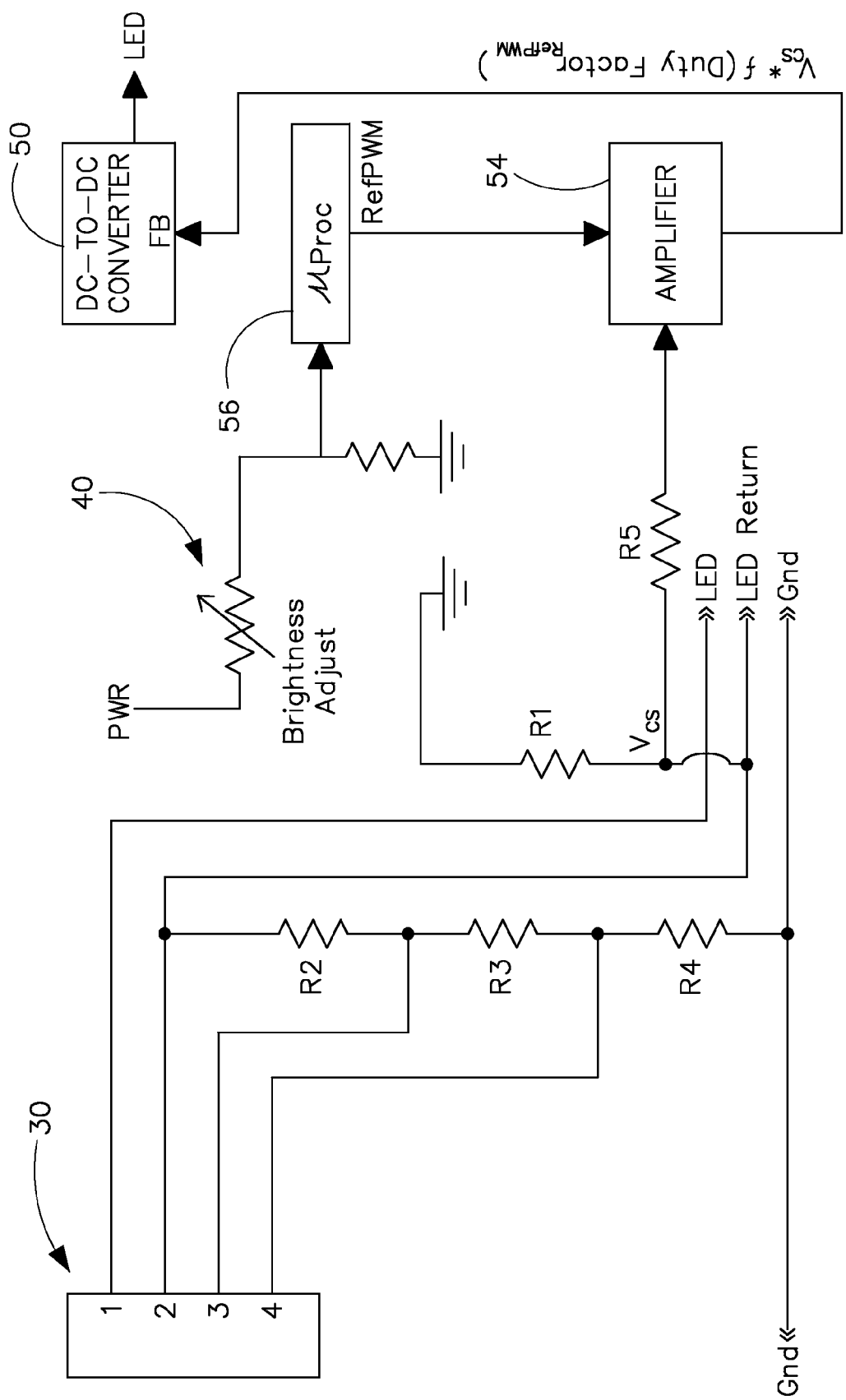
FIG. 8 shows a simplified schematic of the electrical network of the medical headlamp assembly of FIGS. 1-6.

Referring to FIG. 8, a DC-to-DC converter 50 acts as a power supply to whichever one of lamps 18, 18 ' or 18" is connected to jack 30. A feedback loop is formed by the output of converter 50 powering the LED line, all of the current in which flows to the LED return line, and at least a portion of which pass through a current sense resister R1, which in turn drives the feedback pin FB of converter 50. (The modification of the voltage at feedback pin FB through a voltage increase circuit 54 is described below.) The output of converter 50 increases if the voltage of feedback pin FB is below 0.5 volts and decreases if the voltage of feedback pin FB is above 0.5 volts, thereby setting that voltage at pin FB at 0.5 volts. Accordingly, when the voltage increase circuit 54 is not active, the voltage across resister R1 is set at 0.5 volts, and accordingly, $I_{R1}=R1/0.5$ VDC. For the 800 mAmp lamp, for which the return current exits at Pin 2 of the jack 30, a few equations apply:

$$I_{R1} = 800 \text{ mAmps} - I_{R2}$$

$$I_{R1} = \frac{800 \text{ mAmps} * (R_2 + R_3 + R_4)}{R_1 * (R_2 + R_3 + R_4 + 1)}$$

For the 1.1 Amp lamp (from jack 30 pin 3) these equations become:

$$I_{R2,R1} = 1.1 \text{ mAmps} - I_{R3,R4}$$

$$I_{R2,R1} = \frac{1.1 \text{ mAmps} * (R_3 + R_4)}{(R_1 + R_2) * (R_3 + R_4 + 1)}$$

For the 1.4 Amp lamp (from jack 30 pin 4) these equations become:

$$I_{R3,R2,R1} = 1.4 \text{ mAmps} - I_{R4}$$

$$I_{R3,R2,R1} = \frac{1.4 \text{ mAmps} * (R_4)}{(R_1 + R_2 + R_3) * (R_4 + 1)}$$

In addition, for no lamp 18, 18' or 18" may the voltage drop through the lamp and the resistive network composed of $R_1$, $R_2$, $R_3$ and $R_4$ must not exceed a maximum, that in one embodiment is about 3.4 volts. In addition, the power consumption of this resistive network must be minimized for all the lamps, leading to low values for all of the resistors, on the order of a little more than an ohm.

The voltage output of the brightness adjust rheostat 40 is fed into a pin of a microprocessor 56, resulting in a periodic waveform having a duty factor that is related to the rheostat output voltage, appearing on an output pin of the microprocessor 56. When the rheostat 40 is moved to a "dim" setting, this causes microprocessor 56 to produce a waveform that causes voltage increase circuitry 54 to amplify the voltage at its input, thereby reducing the current (and voltage) out of the DC-to-DC converter 50, and reducing the current through resister R5. In an alternative preferred embodiment voltage increase circuitry is set to always amplify its input signal, thereby permitting a lower value for the voltage drop across $R_1$, when the lamp 18, 18' or 18" is not being dimmed. This permits a lower value of resistance for $R_1$, and lower power loss through $R_1$ and through the entire resistance network $R_1$, $R_2$, $R_3$ and $R_4$. For dimming positions of rheostat 40, this amplification is increased.

When the brightness adjust knob 40 is set at its maximum, causing a voltage increase circuit 54 (described below) to pass the voltage from a current sense resister R1, unchanged, then the voltage through the current sense resister R1 is forced to 0.5 volts by the feedback loop implemented by the converter 50 feedback pin FB (driven directly or indirectly by the current sense resister R1, and the converter 50 output powering the lamp 18, 18' or 18", with the LED return line powering resister R1. The While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A medical headlamp assembly, having:
   (a) a headband subassembly, including an electrical network, including a battery and an electrical jack, and a headlamp mount; and
   (b) an electrical headlamp subassembly, having a mounting element matingly and removably engaged to said headlamp mount, and an electrical plug, matingly and removably engaged to said jack and an electrical headlamp, electrically connected to said plug.

2. The medical headlamp assembly of claim 1, wherein said electrical headlamp subassembly is a first electrical headlamp subassembly and further including a second electrical headlamp subassembly, having a mounting element capable of removably mating to said headlamp mount and an electrical plug capable of removably mating to said jack and an electrical headlamp, electrically connected to said plug.

3. The medical headlamp assembly of claim 2, wherein said second electrical headlamp subassembly is different in design from said first electrical headlamp subassembly.

4. The medical headlamp assembly of claim 2, wherein said first electrical headlamp subassembly and said second electrical headlamp subassembly each require an electrical current source at said electrical plug, and wherein said electrical current source required by said second electric headlamp subassembly is different from said electrical current source required by said first electrical headlamp subassembly.

5. The medical headlamp assembly of claim 4, wherein said electrical plug of said first electrical headlamp subassembly is physically identical to said electrical plug of said second electrical headlamp subassembly, each having a set of pin elements, said pin elements being mutually electrically isolated from one another, and wherein in said electrical plug for said first electrical headlamp subassembly a first set of said pin elements are connected to said headlamp, and in said second electrical plug for said second electrical headlamp subassembly a second set of pin elements are connected to said headlamp.

6. The medical headlamp assembly of claim 5, wherein said electrical plugs are audio plugs, each having a single longitudinal element, which is divided into mutually electrically isolated pin elements.

7. The medical headlamp assembly of claim 1, wherein said headlamp subassembly further includes an adjustable mechanical linkage, permitting adjustment of the elevation angle of said electrical headlamp.

8. The medical headlamp assembly of claim 1, wherein said headlamp mount is a guide rod and said mounting element is a slider.

9. The medical headlamp assembly of claim 8, wherein said headband subassembly is shaped to be worn on a human head in a predetermined manner, and wherein when said head is vertically oriented said guide rod is substantially vertical, thereby permitting adjustment of vertical position of said electrical headlamp.

10. A method of switching out a medical headlamp, comprising:
(a) providing a medical headlamp assembly having;
   (i) a headband assembly, including a mounting element, an electrical jack and a power supply assembly electrically connected to said electrical jack;
   (ii) a first headlamp assembly removably engaged to said mounting element and including a conductor terminating in a plug that is plugged into said jack; and
   (iii) a second headlamp assembly removeably engageable to said mounting element and including a conductor terminating in a plug that is engageable to said jack;
(b) removing said first headlamp assembly from said mounting element and unplugging said first headlamp plug from said jack; and
(c) mounting said second headlamp on said mounting element and plugging said second headlamp plug into said jack.

11. The method of claim 10, wherein said second headlamp has different illumination characteristics from said first headlamp.

12. The method of claim 11, wherein said second headlamp has different electrical power requirements from said first lamp.

13. The method of claim 12, wherein said second headlamp plug makes a different electrical connection to said jack, compared to the electrical connection formed by said first headlamp plug to said jack.

14. The method of claim 13, wherein said electrical power supply supplies electrical power having different characteristics to said second headlamp, compared to the characteristics of the electrical power delivered to said first headlamp.

15. The method of claim 14, wherein said power supply assembly includes a network of resisters that the return from the headlamp connects into at a different point, depending on the plug, and includes a power sense resister that drives a DC-to-DC converter, which is driven differently depending on the point in the resistive network where said return from the headlamp is connected to.

16. The method of claim 10, wherein said electrical plugs are audio plugs, each having a single longitudinal element, which is divided into mutually electrically isolated pin elements.

17. The method of claim 10, wherein said headlamp subassembly further includes an adjustable mechanical linkage, permitting adjustment of the elevation angle of said electrical headlamp.

18. The method of claim 10, wherein said headlamp mount is a guide rod and said mounting element is a slider.

19. The method of claim 18, wherein said headband subassembly is shaped to be worn on a human head in a predetermined manner, and wherein when said head is vertically oriented said guide rod is substantially vertical, thereby permitting adjustment of vertical position of said electrical headlamp.

* * * * *